US010285908B2

(12) United States Patent
Mittal et al.

(10) Patent No.: US 10,285,908 B2
(45) Date of Patent: *May 14, 2019

(54) DUAL-CHAMBER PACK

(71) Applicant: Sun Pharmaceutical Industries Limited, Mumbai, Maharashtra (IN)

(72) Inventors: Bhupesh Kumar Mittal, Alwar (IN); Neha Pardal, New Delhi (IN)

(73) Assignee: Sun Pharmaceutical Industries Ltd, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/329,070

(22) PCT Filed: Jul. 30, 2015

(86) PCT No.: PCT/IB2015/055780
§ 371 (c)(1),
(2) Date: Jan. 25, 2017

(87) PCT Pub. No.: WO2016/016845
PCT Pub. Date: Feb. 4, 2016

(65) Prior Publication Data
US 2017/0216142 A1      Aug. 3, 2017

(30) Foreign Application Priority Data
Jul. 30, 2014   (IN) .......................... 2149/DEL/2014

(51) Int. Cl.
*B65D 41/34*      (2006.01)
*A61J 1/20*       (2006.01)
(Continued)

(52) U.S. Cl.
CPC .......... *A61J 1/2093* (2013.01); *A61J 1/2027* (2015.05); *A61J 7/0046* (2013.01); *A61K 9/0053* (2013.01);
(Continued)

(58) Field of Classification Search
CPC ..... A64J 1/2093; A64J 1/2027; A61K 9/0053; B65D 41/34; B65D 51/2835
(Continued)

(56) References Cited

U.S. PATENT DOCUMENTS 3,156,369 A    11/1964   Bowes et al. ..................... 215/6
3,603,469 A     9/1971   Magni .............................. 215/6
(Continued)

FOREIGN PATENT DOCUMENTS

CH         567978      8/1975
EP       0 601 508 B1  3/1999
(Continued)

OTHER PUBLICATIONS

Lopez-Liuchi et al., "Therapy for type 2 diabetes: where do we stand after the UK Prospective Diabetes Study?," *European Journal of Endocrinology*, 140:4-6 (1999).
(Continued)

*Primary Examiner* — King M Chu
(74) *Attorney, Agent, or Firm* — Stanley Liang; Liang Frank, LLP

(57) ABSTRACT

The present invention relates to a dual-chamber pack for a multi-dose oral liquid pharmaceutical composition wherein the compositions of the first and second chambers are mixed at the time of first administration.

9 Claims, 3 Drawing Sheets

(51) Int. Cl.
*A61J 7/00* (2006.01)
*B65D 51/28* (2006.01)
*A61K 9/00* (2006.01)

(52) U.S. Cl.
CPC .......... *B65D 41/34* (2013.01); *B65D 51/285* (2013.01); *B65D 51/2835* (2013.01)

(58) Field of Classification Search
USPC .............................................. 206/222, 219
See application file for complete search history.

(56) References Cited

U.S. PATENT DOCUMENTS

| | | | |
|---|---|---|---|
| 3,632,645 A | 1/1972 | Bream et al. ................. | 260/558 |
| 3,687,076 A | 8/1972 | Friant et al. | |
| 3,840,136 A | 10/1974 | Lanfranconi et al. ............ | 215/6 |
| 3,917,063 A | 11/1975 | Chibret et al. | |
| 4,024,952 A | 5/1977 | Leitz | |
| 4,982,875 A | 1/1991 | Pozzi et al. ...................... | 222/83 |
| 5,058,770 A | 10/1991 | Herold et al. ................... | 222/80 |
| 5,170,888 A | 12/1992 | Goncalves | |
| 5,273,760 A | 12/1993 | Oshlack et al. ............ | 424/480 |
| 5,419,445 A | 5/1995 | Kaesemeyer ................ | 215/11.1 |
| 5,431,915 A | 7/1995 | Harvey et al. ................ | 424/439 |
| 5,460,828 A | 10/1995 | Santus et al. | |
| 5,472,712 A | 12/1995 | Oshlack et al. ............ | 424/480 |
| 5,854,290 A | 12/1998 | Arnsten et al. ............. | 514/617 |
| 5,955,106 A | 9/1999 | Moeckel et al. | |
| 6,148,996 A | 11/2000 | Morini ......................... | 206/222 |
| 6,156,340 A | 12/2000 | Adeyeye et al. ............ | 424/463 |
| 6,287,599 B1 | 9/2001 | Burnside et al. ............ | 424/468 |
| 6,676,966 B1 | 1/2004 | Odidi et al. ................. | 424/464 |
| 6,811,794 B2 | 11/2004 | Burnside et al. ............ | 424/468 |
| 6,890,957 B2 | 5/2005 | Chandran et al. ........... | 514/634 |
| 7,214,387 B2 | 5/2007 | Sanghvi et al. ............. | 424/468 |
| 7,748,550 B2 | 7/2010 | Cho | |
| 7,906,145 B2 | 3/2011 | Castan et al. ............... | 424/489 |
| 8,002,734 B2 | 8/2011 | Bassarab et al. ............. | 604/82 |
| 8,197,850 B2 | 6/2012 | Castan et al. ............... | 424/489 |
| 8,297,456 B1 | 10/2012 | Anderson ..................... | 215/227 |
| 8,318,210 B2 | 11/2012 | Tengler et al. .............. | 424/501 |
| 8,453,833 B2 | 6/2013 | Porter | |
| 8,491,935 B2 | 7/2013 | Mehta et al. ................ | 424/487 |
| 8,541,018 B2 | 9/2013 | Radke et al. ................ | 424/439 |
| 8,960,424 B1 | 2/2015 | Anderson | |
| 9,132,950 B1 | 9/2015 | Anderson et al. | |
| 2001/0032643 A1* | 10/2001 | Hochrainer .......... | A61K 9/0078 128/200.21 |
| 2003/0171407 A1 | 9/2003 | Freese et al. ................ | 514/342 |
| 2003/0199846 A1 | 10/2003 | Fowles et al. ............... | 604/403 |
| 2004/0062800 A1 | 4/2004 | Burnside et al. ............ | 424/468 |
| 2004/0062802 A1 | 4/2004 | Hermelin ..................... | 424/468 |
| 2004/0109891 A1 | 6/2004 | Sanghvi et al. ............. | 424/468 |
| 2007/0193894 A1* | 8/2007 | Macken ............. | B65D 81/3222 206/219 |
| 2008/0008765 A1 | 1/2008 | Schwarz et al. ............ | 424/493 |
| 2008/0095855 A1 | 4/2008 | Schwarz | |
| 2008/0118570 A1 | 5/2008 | Liu et al. ..................... | 424/490 |
| 2008/0124432 A1 | 5/2008 | Ma | |
| 2008/0202950 A1 | 8/2008 | Anderson .................... | 206/219 |
| 2008/0314775 A1 | 12/2008 | Owoc | |
| 2009/0123538 A1 | 5/2009 | Alani et al. .................. | 424/464 |
| 2009/0142378 A1 | 6/2009 | Frisbee ......................... | 424/400 |
| 2009/0176691 A1 | 7/2009 | Bennis et al. .................. | 514/3 |
| 2009/0325938 A1 | 12/2009 | Lichter et al. ............... | 514/220 |
| 2010/0092562 A1 | 4/2010 | Hollenbeck et al. ......... | 424/488 |
| 2010/0282624 A1 | 11/2010 | Paganuzzi | |
| 2010/0330150 A1 | 12/2010 | Venkatesh et al. ........... | 424/439 |
| 2011/0268808 A1 | 11/2011 | Jain et al. | |
| 2011/0313046 A1 | 12/2011 | Ermer ......................... | 514/617 |
| 2012/0178666 A1 | 7/2012 | Franklin et al. ............. | 514/1.3 |
| 2012/0220930 A1* | 8/2012 | Griffiths ............. | A61M 5/2033 604/89 |
| 2013/0109659 A1 | 5/2013 | Soler Ranzani et al. ..... | 514/158 |
| 2014/0050796 A1 | 2/2014 | Tengler et al. ............... | 424/494 |
| 2014/0309271 A1 | 10/2014 | Price | |
| 2014/0319141 A1 | 10/2014 | Stratis et al. ................. | 220/277 |
| 2015/0021214 A1 | 1/2015 | Besic et al. | |
| 2016/0228360 A1 | 8/2016 | Kumar et al. | |
| 2016/0228379 A1 | 8/2016 | Kumar et al. | |
| 2016/0271070 A1 | 9/2016 | Singh et al. | |
| 2016/0317388 A1 | 11/2016 | Bhargava et al. | |
| 2016/0346233 A1 | 12/2016 | Singh et al. | |
| 2016/0346235 A1 | 12/2016 | Singh et al. | |
| 2017/0119627 A1 | 1/2017 | Gambino et al. | |
| 2017/0216142 A1 | 8/2017 | Mittal et al. | |
| 2017/0304234 A1 | 10/2017 | Singh et al. | |
| 2017/0312177 A1 | 11/2017 | Bhargava et al. | |

FOREIGN PATENT DOCUMENTS

| | | | |
|---|---|---|---|
| EP | 1122186 | 8/2001 | |
| EP | 1 140 027 | 10/2005 | ............... A61K 9/16 |
| FR | 2 897 267 B1 | 2/2016 | |
| JP | 2012/514632 | 6/2012 | |
| NO | 2005/097040 A1 | 10/2005 | |
| WO | WO 00/38655 | 7/2000 | ............... A61K 9/16 |
| WO | WO 2006/030297 | 3/2003 | ............... A61K 9/16 |
| WO | WO 2004/012715 A1 | 2/2004 | |
| WO | WO 2006/086856 A1 | 8/2006 | |
| WO | WO 2008/122993 | 10/2008 | ............... A61K 9/16 |
| WO | WO 2010/045656 A3 | 4/2010 | |
| WO | WO 2011/077451 | 6/2011 | ............... A61K 9/28 |
| WO | WO 2011/107855 | 9/2011 | ............... A61K 9/50 |
| WO | WO 2011/150506 | 12/2011 | ............... A61K 9/48 |
| WO | WO 2012052853 A3 | 4/2012 | |
| WO | WO 2012/063257 | 5/2012 | ............ A61K 47/30 |
| WO | WO 2013043064 | 3/2013 | |
| WO | WO 2013091882 A1 | 6/2013 | |
| WO | WO 2014/174119 | 10/2014 | ............ A61K 31/155 |
| WO | WO 2015/166472 A1 | 11/2015 | |
| WO | WO 2015/166473 A1 | 11/2015 | |
| WO | WO 2016/178130 A1 | 11/2016 | |
| WO | WO 2016/178131 A1 | 11/2016 | |
| WO | WO 2016/178132 A1 | 11/2016 | |
| WO | WO 2017/182851 A1 | 10/2017 | |
| WO | WO 2017/182852 A1 | 10/2017 | |
| WO | WO 2017/191485 A1 | 11/2017 | |

OTHER PUBLICATIONS

Murtaza,"Ethylcellulose Microparticles: A Review," *Drug Research*, 69(1):11-22 (2012).
Co-pending PCT Application No. PCT/IB2015/053207 filed May 1, 2015, published as WO 2015/166472 on Nov. 5, 2015.
International Search Report and Written Opinion for International Application No. PCT/IB2015/053207, issued by US/ISA dated Aug. 7, 2015.
International Preliminary Report on Patentability for International Application No. PCT/162015/053207, issued by WIPO dated Mar. 16, 2016.
Co-pending U.S. Appl. No. 15/133,773 filed Apr. 20, 2016, published as U.S. 2016/0228360 on Aug. 11, 2016.
Restriction Requirement for U.S. Appl. No. 15/133,773, issued by USPTO dated Jun. 10, 2016.
Office Action for U.S. Appl. No. 15/133,773, issued by USPTO dated Jul. 27, 2016.
Final Office Action for U.S. Appl. No. 15/133,773, issued by USPTO dated Dec. 16, 2016.
Final Office Action for U.S. Appl. No. 15/133,773, issued by USPTO dated Apr. 13, 2017.
Co-pending PCT Application No. PCT/IB2016/052484 filed May 2, 2016, published as WO 2016/178130 on Nov. 10, 2016.
International Search Report and Written Opinion for International Application No. PCT/IB2016/052484, issued by US/ISA dated Sep. 8, 2016.
Co-pending U.S. Appl. No. 15/144,000 filed May 2, 2016, not yet published.
Office Action for U.S. Appl. No. 15/144,000, issued by USPTO dated Jun. 23, 2016.

(56) References Cited

OTHER PUBLICATIONS

Final Office Action for U.S. Appl. No. 15/144,000, issued by USPTO dated Nov. 4, 2016.
Office Action for U.S. Appl. No. 15/144,000, issued by USPTO dated Feb. 14, 2017.
Restriction Requirement for U.S. Appl. No. 15/133,826, issued by USPTO dated Jun. 23, 2016.
Final Office Action for U.S. Appl. No. 15/133,826, issued by USPTO dated Dec. 20, 2016.
Office Action for U.S. Appl. No. 15/133,826, issued by USPTO dated Feb. 14, 2017.
Restriction Requirement for U.S. Appl. No. 15/148,069, issued by USPTO dated Jul. 21, 2016.
Final Office Action for U.S. Appl. No. 15/148,069, issued by USPTO dated Mar. 20, 2017.
Final Office Action for U.S. Appl. No. 15/148,131 issued by USPTO dated Apr. 5, 2017.
Final Office Action for U.S. Appl. No. 15/144,026, issued by USPTO dated Apr. 6, 2017.
Co-pending PCT Application No. PCT/IB2015/055780 filed Jul. 30, 2015, published as WO 2016/016845 on Feb. 4, 2016.
International Search Report and Written Opinion for International Application No. PCT/IB2015/055780, issued by US/ISA dated Dec. 7, 2015.
International Preliminary Report on Patentability for International Application No. PCT/IB2015/055780, issued by WIPO dated Feb. 9, 2017.
Restriction Requirement for US Appl. No. 15/144,058, issued by USPTO dated Sep. 30, 2016.
Office Action for U.S. Appl. No. 15/144,058, issued by USPTO dated Dec. 16, 2016.
Office Action for U.S. Appl. No. 15/144,058, issued by USPTO dated May 11, 2017.
Office Action for U.S. Appl. No. 15/352,993, issued by USPTO dated Mar. 24, 2017.
Co-pending PCT Application No. PCT/IB2016/052488 filed May 2, 2016, not yet published.
International Search Report and Written Opinion for International Application No. PCT/IB2016/052488, issued by US/ISA dated Aug. 31, 2016.
Co-pending U.S. Appl. No. 15/144,098, filed May 2, 2016, not yet published.
Kristine, "EKG Results/Tenex", Dr. Mom's Spot (Mar. 26, 2010) Available: http://drmomsspot.blogspot.com/2010/03/ekg-results-tenex.html.
Co-pending PCT Application No. PCT/IB2015/053209 filed May 1, 2015.
International Search Report and Written Opinion for International Application No. PCT/IB2015/053209, issued by PCT dated Aug. 14, 2015.
International Preliminary Report on Patentability for International Application No. PCT/IB2015/053209, issued by PCT dated Nov. 10, 2016.
Co-pending U.S. Appl. No. 15/133,826, filed Apr. 20, 2016.
Office Action for U.S. Appl. No. 15/133,826, issued by USPTO dated Jul. 28, 2016.
Co-pending PCT Application No. PCT/IB2016/052604 filed May 6, 2016.
International Search Report and Written Opinion for International Application No. PCT/IB2016/052604, issued by PCT dated Aug. 31, 2016.
Co-pending U.S. Appl. No. 15/148,069, filed May 6, 2016.
Office Action for U.S. Appl. No. 15/148,069, issued by USPTO dated Nov. 2, 2016.
Co-pending PCT Application No. PCT/IB2016/052607 filed May 6, 2016.
International Search Report and Written Opinion for International Application No. PCT/IB2016/052607, issued by PCT dated Sep. 2, 2016.
Co-pending U.S. Appl. No. 15/148,131, filed May 6, 2016.

Office Action for U.S. Appl. No. 15/148,131, issued by USPTO dated Oct. 7, 2016.
Co-pending PCT Application No. PCT/IB2016/052485 filed May 2, 2016.
International Search Report and Written Opinion for International Application No. PCT/IB2016/052485, issued by PCT dated Aug. 31, 2016.
Co-pending U.S. Appl. No. 15/144,026, filed May 2, 2016.
Office Action for U.S. Appl. No. 15/144,026, issued by USPTO dated Oct. 12, 2016.
Co-pending PCT Application No. PCT/IB2016/052486 filed May 2, 2016.
International Search Report and Written Opinion for International Application No. PCT/IB2016/052486, issued by PCT dated Sep. 9, 2016.
Co-pending U.S. Appl. No. 15/144,058, filed May 2, 2016.
Co-pending U.S. Appl. No. 15/352,993, filed Nov. 16, 2016.
Steeman, 2009. *Innovative dispensing bottle caps for sensitive vitamins* [online]. Best In Packaging. Available from: http://bestinpackaging.com/2009/05/29/innovative-dispensing-bottle-caps-for-sensitive-vitamins/.
Intuiv: Highlights of prescribing information (201 X Shire US Inc, Revised Feb. 2013).
Medela Breast Milk Bottle Set, Target, published on or before 2010. Available from: www.target.com/p/medela-breast-milk-set-8oz-3ct/-/A-11189915 (Accessed on: Aug. 14, 2017).
Final Office Action for U.S. Appl. No. 15/144,058, issued by USPTO dated Jul. 21, 2017.
Office Action for U.S. Appl. No. 15/144,098, issued by USPTO dated Jul. 13, 2017.
Office Action for U.S. Appl. No. 15/133,773, issued by USPTO dated Aug. 1, 2017.
Office Action for U.S. Appl. No. 15/148,069, issued by USPTO dated Aug. 10, 2017.
Office Action for U.S. Appl. No. 15/144,026, issued by USPTO dated Aug. 24, 2017.
Office Action for U.S. Appl. No. 15/148,131, issued by USPTO dated Sep. 29, 2017.
Office Action for U.S. Appl. No. 15/352,993, issued by USPTO dated Aug. 24, 2017.
Final Office Action for U.S. Appl. No. 15/144,000, issued by USPTO dated Aug. 24, 2017.
Continuation U.S. Appl. No. 15/800,682, filed Nov. 1, 2017, not yet published.
International Preliminary Report on Patentability for International Application No. PCT/IB2016/052485, issued by WIPO dated Nov. 16, 2017.
International Preliminary Report on Patentability for International Application No. PCT/IB2016/052484, issued by WIPO dated Nov. 16, 2017.
International Preliminary Report on Patentability for International Application No. PCT/IB2016/052486, issued by WIPO dated Nov. 16, 2017.
Final Office Action for U.S. Appl. No. 15/133,773, issued by USPTO dated Dec. 11, 2017.
Restriction Requirement for U.S. Appl. No. 15/800,682, issued by USPTO dated Dec. 15, 2017.
Office Action for U.S. Appl. No. 15/144,058, issued by USPTO dated Jan. 16, 2018.
U.S. Appl. No. 15/853,219, filed Dec. 22, 2017, not yet published.
Final Office Action for U.S. Appl. No. 15/148,069, issued by USPTO dated Jan. 19, 2018.
Final Office Action for U.S. Appl. No. 15/352,993, issued by USPTO dated Feb. 8, 2018.
Final Office Action for U.S. Appl. No. 15/144,026, issued by USPTO dated Feb. 7, 2018.
Final Office Action for U.S. Appl. No. 15/133,826, issued by USPTO dated Feb. 12, 2018.
Final Office Action for U.S. Appl. No. 15/144,098, issued by USPTO dated Feb. 22, 2018.
U.S. Appl. No. 15/942,711, filed Apr. 2, 2018, not yet published.
U.S. Appl. No. 15/942,840, filed Apr. 2, 2018, not yet published.

(56) References Cited

OTHER PUBLICATIONS

Office Action for AU Application No. 2017279809, issued by AU PTO dated Jun. 1, 2018.
Office Action for AU Application No. 2017254908, issued by AU PTO dated Jun. 1, 2018.
EP Extended Search Report dated Feb. 16, 2018 for European Patent Application No. 15827750.9.
Final Office Action for U.S. Appl. No. 15/148,131, issued by USPTO dated Aug. 6, 2018.
European Extended Search Report dated Jun. 6, 2018 for European Patent Application No. 17210326.9.
Office Action for U.S. Appl. No. 15/144,000, issued by USPTO dated Aug. 31, 2018.
Office Action for U.S. Appl. No. 15/800,682, issued by USPTO dated Apr. 10, 2018.
Office action issued Dec. 11, 2018 for JP Application No. 2017-508782.
EESR issued on Nov. 9, 2018 for EP Application No. 16789381.7.

* cited by examiner

DUAL-CHAMBER PACK

FIELD OF THE INVENTION

The present invention relates to a dual-chamber pack for a multi-dose oral liquid pharmaceutical composition wherein the compositions of the first and second chambers are mixed at the time of first administration.

BACKGROUND OF THE INVENTION

Liquid pharmaceutical compositions are generally used in patients having difficulty in swallowing solid dosage forms, in particular pediatric or geriatric patients. These compositions are further advantageous because the dose of the drug may be adjusted easily to meet the patient's requirement. Further, such compositions are a viable option for formulating water-insoluble or poorly-soluble drugs. In addition, the bitter taste of drugs can be reduced by formulating them in the form of a suspension.

Liquid pharmaceutical compositions commonly have the drug dissolved or suspended in water or another liquid diluent. However, certain drugs are susceptible to degradation in the presence of water or other aqueous mediums. In conventional packs, to minimize the degradation in the presence of water, the drug is placed inside the bottle and is formulated by the addition of a liquid diluent or water at the time of administration by the patient, which makes it susceptible to administration errors and contamination.

U.S. Pat. No. 8,002,734 discloses a dual-chamber container for an injectable composition comprising a solid lyophilizate and a liquid reconstituting medium thereof, wherein the cylindrical body has a closure at each of two ends. One of the ends allows for reconstitution and the other end allows for administration by injection.

U.S. Pat. No. 4,982,875 discloses a cap, a reservoir, and a dispensing dropper assembly package wherein a reservoir having reduced thickness at the bottom is inserted internally on the upper mouth of the container for an ophthalmic composition. The cap helps to push the delivery piston downwards by a screw-based mechanism, which in turn cuts the bottom of the reservoir at all points except one, where the bottom remains attached to the reservoir.

SUMMARY OF THE INVENTION

The present invention provides an alternative pack for a multi-dose oral liquid pharmaceutical composition comprising of two chambers, wherein the pack is adaptable for low to high dose drugs. The pack allows the patient ease of dispensing with only a few simple steps required for reconstitution.

The present invention provides a dual-chamber pack for a multi-dose oral liquid pharmaceutical composition comprising of:
(a) a first chamber in the form of a container (8) provided with an opening (7) at an upper end, comprising a liquid vehicle containing one or more pharmaceutically acceptable inert excipients;
(b) a second chamber comprising:
(i) a plunger (3) adapted to fit into a plug (4) having a top flat surface, containing a solid composition comprising a drug in an amount of from about 50 mg to about 130 g and optionally one or more pharmaceutically acceptable inert excipients; and
(ii) the plug (4), with a breakable polymeric membrane (5), adapted to fit into the opening (7) from a lower end and into a cap (1) from the upper end; and
(c) the cap (1) over the second chamber comprising a means to exert pressure onto the plunger (3) so as to partially rupture the breakable polymeric membrane (5) of the plug (4) and deliver the solid composition into the container (8)
wherein the compositions of both chambers are mixed at the time of first administration by applying pressure on the cap (1).

DETAILED DESCRIPTION OF THE INVENTION

Figure 1:
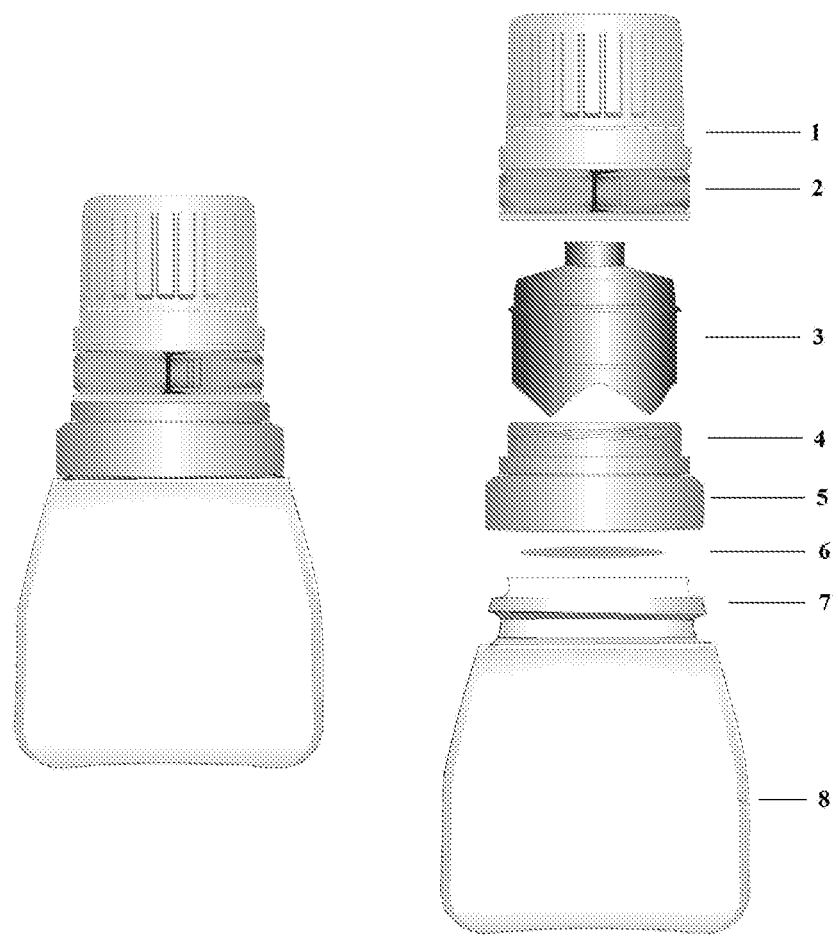
FIG. 1: Schematic diagram of the components of a dual-chamber pack wherein a dome-shaped plunger (3) ruptures the polymeric membrane (5) by a screw-based mechanism.

A first aspect of the present invention relates to dual-chamber pack for a multi-dose oral liquid pharmaceutical composition comprising of:
(a) a first chamber in the form of a container (8) provided with an opening (7) at an upper end comprising a liquid vehicle containing one or more pharmaceutically acceptable inert excipients;
(b) a second chamber comprising:
(i) a plunger (3) adapted to fit into a plug (4) having a top flat surface, containing a solid composition comprising a drug in an amount of from about 50 mg to about 130 g and optionally one or more pharmaceutically acceptable inert excipients; and
(ii) the plug (4), with a breakable polymeric membrane (5), adapted to fit into an opening (7) from a lower end and into a cap (1) from the upper end; and
(c) the cap (1) over the second chamber comprising a means to exert pressure onto the plunger (3) so as to partially rupture the breakable polymeric membrane (5) of the plug (4) and deliver the solid composition into the container (8)
wherein the compositions of both chambers are mixed at the time of first administration by applying pressure on the cap (1).

The term "multi-dose" as used herein, refers to a drug product which is to be administered in multiple doses after reconstitution, over a period of time varying from 1 day to 1 month, in particular from 1 week to 1 month.

The reconstituted composition is stable for a period of 1 month whereby the multiple doses are administered as per the dosing schedule of the drug. In particular, stability studies were carried out for metformin powder for oral suspension and cefprozil powder for oral suspension. Both of the liquid compositions, after being reconstituted, were found to be stable for at least one month.

The term "stable" as used herein, refers to no significant changes in the drug product with respect to assay, viscosity, and total related substances, including highest unknown impurity, when subjected to stability conditions of 40° C. and 75% RH for 1 month before and after reconstitution.

According to another embodiment of this aspect, the reconstituted liquid pharmaceutical composition is stable when exposed to stability conditions of 40° C. and 75% RH for a period of 1 month.

According to one embodiment of this aspect, the container (8) is in the form of a glass or a plastic or a metallic bottle. The first chamber may be sealed at the opening (7) of the container (8) using a heat seal or a pressure seal or an induction seal using a bottle liner (6). This liner provides protection against any spill from the first chamber during manufacturing as well as storage. Also, it acts as an enhanced barrier for ingression of moisture from the first chamber to the second chamber.

According to another embodiment of this aspect, the multi-dose oral liquid composition is in the form of a suspension or a solution dosage form. In case of a suspension, the solid composition of the second chamber is dispersed into the liquid vehicle of the first chamber at the time of first administration. In case of a solution, the solid composition of the second chamber is dissolved in the liquid vehicle of the first chamber at the time of first administration.

According to another embodiment of this aspect, the liquid vehicle of the first chamber may comprise purified water or a mixture of purified water and one or more suitable organic solvents. The organic solvents may be selected from the group consisting of ethanol, glycerin, propylene glycol, polyethylene glycol, and mixtures thereof. The amount of the liquid composition may vary from about 5 mL to about 350 mL.

The liquid composition of the first chamber may further comprise pharmaceutically acceptable inert excipients selected from the group consisting of surfactants, wetting agents, thickening agents, anti-oxidants, sweeteners, buffering agents, osmotic agents, preservatives, coloring agents, and mixtures thereof.

According to another embodiment of this aspect, the solid composition of the second chamber comprising a drug is in the form of powder, paste, beads, granules, gel, or a compressed tablet. The compressed tablet may be a tablet for oral suspension. The solid composition may be formulated into a suitable form using pharmaceutically acceptable inert excipients selected from the group consisting of surfactants, wetting agents, anti-oxidants, buffering agents, preservatives, coloring agents, lubricants, diluents, disintegrants, and mixtures thereof.

According to another embodiment of this aspect, the drug in the second chamber is a soluble, a water-insoluble, or a poorly-soluble drug. The drug may have a stability problem due to which the drug is reconstituted using a liquid composition at the time of administration. This dual-chamber pack can be used for drugs such as valacyclovir, metformin, azithromycin, cloxacillin, clarithromycin, erythromycin, amoxicillin alone or in combination with clavulanic acid, cefdinir, cefuroxime axetil, cefixime, cefadroxil, cefpodoxime, cefaclor, cefprozil, fluconazole, voriconazole, acarbose, miglitol, voglibose, repaglinide, nateglinide, glibenclamide, glimepride, glipizide, gliclazide, chloropropamide, tolbutamide, phenformin, alogliptin, sitagliptin, linagliptin, saxagliptin, rosiglitazone, pioglitazone, troglitazone, faraglitazar, englitazone, darglitazone, isaglitazone, zorglitazone, liraglutide, muraglitazar, peliglitazar, tesaglitazar, canagliflozin, dapagliflozin, remogliflozin, sergliflozin, verapamil, albuterol, salmeterol, acebutolol, sotalol, penicillamine, norfloxacin, ciprofloxacin, ofloxacin, levofloxacin, moxifloxacin, trovafloxacin, gatifloxacin, tetracycline, demeclocycline hydrochloride, losartan, irbesartan, eprosartan, valsartan, diltiazem, isosorbide mononitrate, ranolazine, propafenone, hydroxyurea, hydrocodone, delavirdine, pentosan polysulfate, abacavir, amantadine, acyclovir, ganciclovir, valganciclovir, saquinavir, indinavir, nelfinavir, lamivudine, didanosine, zidovudine, nabumetone, celecoxib, mefenamic acid, naproxen, propoxyphene, cimetidine, ranitidine, albendazole, mebendazole, thiobendazole, pyrazinamide, praziquantel, chlorpromazine, sumatriptan, bupropion, aminobenzoate, pyridostigmine bromide, potassium chloride, niacin, tocainide, quetiapine, fexofenadine, sertraline, chlorpheniramine, rifampin, methenamine, nefazodone, modafinil, metaxalone, morphine, sevelamer, lithium carbonate, flecainide acetate, simethicone, methyldopa, chlorthiazide, metyrosine, procainamide, entacapone, metoprolol, propanolol hydrochloride, chlorzoxazone, tolmetin, tramadol, bepridil, phenytoin, gabapentin, terbinafine, atorvastatin, doxepine, rifabutin, mesalamine, etidronate, nitrofurantoin, choline magnesium trisalicylate, theophylline, nizatidine, methocarbamol, mycophenolate mofetil, tolcapone, ticlopidine, capecitabine, orlistat, colsevelam, meperidine, hydroxychloroquine, guaifenesin, guanfacine, amiodarone, quinidine, atomoxetine, felbamate, pseudoephedrine, carisoprodol, venlafaxine, etodolac, chondroitin, lansoprazole, pantoprazole, esomeprazole, dexlansoprazole, dexmethylphenidate, methylphenidate, sodium oxybate, isotretinoin, oseltamivir, cholestyramine, nystatin, and a combination of artemether and lumefantrine. This dual-chamber pack is suitable for both low dose and high dose drugs. The dose of the drug may vary between about 50 mg and about 130 g.

Figure 2:
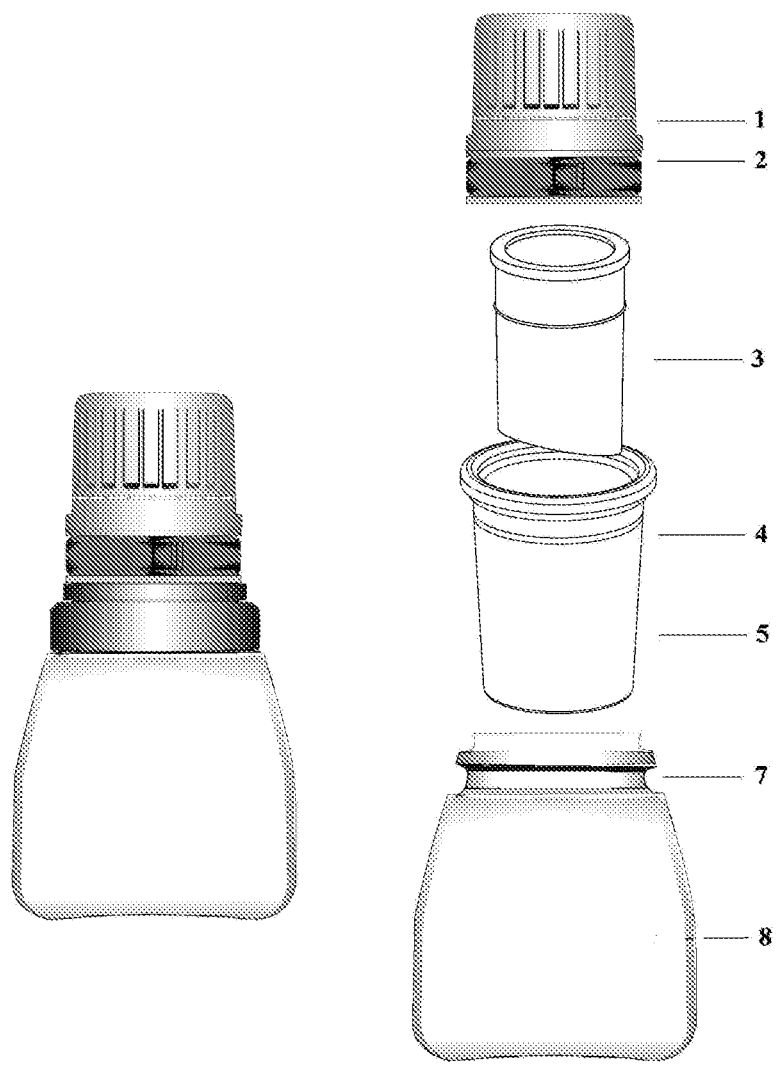
FIG. 2: Schematic diagram of the components of a dual-chamber pack wherein a flute-shaped plunger (3) fitted in a snuggly fitted plug (4) ruptures the polymeric membrane (5) by a screw-based mechanism.
Figure 3:
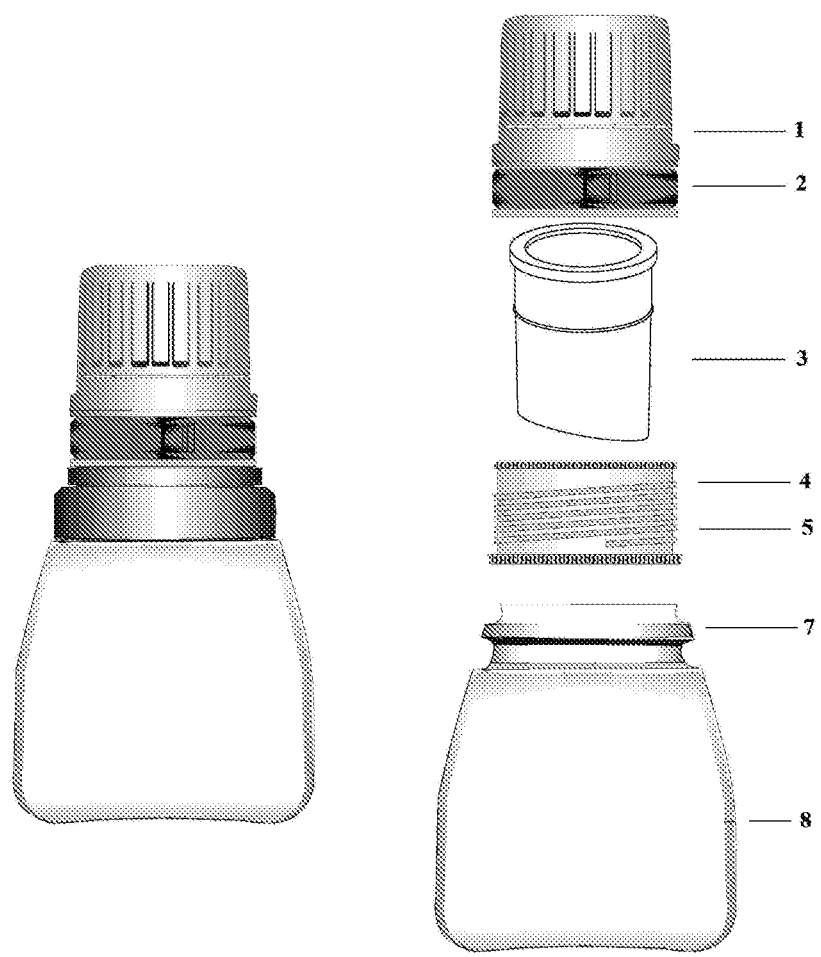
FIG. 3: Schematic diagram of the components of the dual-chamber pack wherein a flute-shaped plunger (3) fitted in a screw fitted plug (4) ruptures the polymeric membrane (5) by a screw-based mechanism.

According to another embodiment of this aspect, the plunger (3) is inversely fitted into the plug (4) which is subsequently screwed or snuggly fitted on the opening (7) of the container (8). The plunger (3) may be screwed or snuggly fitted into the plug (4). The plunger (3) may be flute shaped (as in FIGS. 2 and 3) or may exhibit two or more projections (as in FIG. 1) to rupture the polymeric membrane (5). The plug (4) and the plunger (3) may be made up of a plastic or a metallic material.

According to another embodiment of this aspect, the compositions of the first and second chambers of the container are separated by a polymeric membrane (5) of the plug (4) which is easily breakable. The plunger (3) helps to rupture the polymeric membrane (5) upon the application of pressure by a screw-based mechanism. When pressure is applied on the cap (1), not more than three-fourths of the circumference of the polymeric membrane (5) is ruptured by the plunger (3). The intact polymeric membrane remains attached to the circumference of the plug. In cases where a bottle liner (6) exists between the first and the second chambers, the plunger (3) would break the bottle liner (6) in the same manner as it ruptures the polymeric membrane (5). The unabridged part of the bottle liner (6) remains attached to the opening (7) of the container (8).

According to another embodiment of this aspect, the dual-chamber pack further comprises a cap (1) with a tamper-evident tear band (2). The cap (1), upon application of pressure by a screw-based mechanism, pushes the plunger (3) downwards, which in turn ruptures the polymeric membrane (5) allowing the contents of two chambers to be mixed. The cap (1) may be designed to have child-resistant properties.

The term "tamper-evident tear band" as used herein, refers to a band attached co-axially to the cap (1) from above. The band breaks easily on pulling apart. The tamper-evident tear band (2) ensures the overall integrity of the product until the time of first administration.

A second aspect of the present invention provides a method of providing a multi-dose oral liquid pharmaceutical composition in a dual-chamber pack, comprising the steps of:

a) providing a container (8) comprising a first chamber, a second chamber, and a cap (1);
b) filling the first chamber partially with a liquid vehicle;
c) filling a plunger (3) of the second chamber at least partially with a solid composition comprising the drug;
d) fixing the plunger (3) into a plug (4) of the second composition and mounting the plug (4) on an opening (7) of the first chamber;
e) activating the dual-chamber pack at the time of first administration by screwing the cap (1) so that the plunger (3) ruptures three-fourths of the circumference of a polymeric membrane (5) (as given in FIG. 1); and
f) shaking the container to allow the mixing of the two compositions to obtain the liquid pharmaceutical composition.

The term "about" as used herein, refers to any value which lies within the range defined by a variation of up to ±10% of the value.

We claim:

1. A dual-chamber pack for a multi-dose oral liquid pharmaceutical composition comprising of:
    (a) a first chamber in the form of a container (8) provided with an opening (7) at an upper end, comprising a liquid vehicle containing one or more pharmaceutically acceptable inert excipients; and
    (b) a second chamber comprising:
    (i) a plunger (3) adapted to fit into a plug (4) having a top flat surface, containing a solid composition comprising a drug in an amount of from about 50 mg to about 130 g and one or more pharmaceutically acceptable inert excipients; and
    (ii) a plug (4), with a breakable polymeric membrane (5), adapted to fit into the opening (7) from a lower end and into a cap (1) from the upper end; and
    (c) the cap (1) over the second chamber comprising a means to exert pressure onto the plunger (3) so as to partially rupture the breakable polymeric membrane (5) of the plug (4) and deliver the solid composition into the container (8)

wherein the compositions of both chambers are mixed at the time of first administration by applying pressure on the cap (1) and the plunger (3) is activated by a screw-based mechanism and the reconstituted oral liquid pharmaceutical composition formed after mixing for first administration is stable at 40° C. and 75% RH for a period of at least 1 month.

2. The dual-chamber pack according to claim 1, wherein the liquid vehicle is present in an amount of from about 5 mL to about 350 mL.

3. The dual-chamber pack according to claim 1, wherein the solid composition of the second chamber is in the form of a powder, a paste, beads, granules, gel, or a compressed tablet.

4. The dual-chamber pack according to claim 1, wherein the multi-dose oral liquid pharmaceutical composition is in the form of a suspension or a syrup dosage form.

5. The dual-chamber pack according to claim 1, wherein the plug (4) may be screwed or snuggly fitted onto the opening (7) of the container (8).

6. The dual-chamber pack according to claim 1, wherein the plunger (3) may be flute shaped or may exhibit two or more sharp projections.

7. The dual-chamber pack according to claim 1, wherein the plunger (3) is inversely fitted into the plug (4) and the plug (4) is then mounted on the opening (7) of the container (8).

8. The dual-chamber pack according to claim 1, wherein not more than three-fourths of the circumference of the polymeric membrane (5) is ruptured by the plunger (3) when pressure is applied on the cap (1).

9. The dual-chamber pack according to claim 1, wherein the cap (1) further comprises a tamper-evident tear band (2).

* * * * *